United States Patent [19]

Kaschuba et al.

[11] 4,032,603

[45] June 28, 1977

[54] PRODUCTION OF PHOSPHORUS OXY COMPOUNDS

[75] Inventors: Johannes Kaschuba, Odenthal-Gloebusch; Manfred Ernst, Leverkusen, both of Germany

[73] Assignee: Bayer Aktiengesellschaft, Leverkusen, Germany

[22] Filed: Jan. 23, 1976

[21] Appl. No.: 651,985

[30] Foreign Application Priority Data

Feb. 22, 1975  Germany .......................... 2507730

[52] U.S. Cl. .......................... 260/990; 260/606.5 P
[51] Int. Cl.² ...................... C07F 9/11; C07F 9/32; C07F 9/40; C07F 9/53
[58] Field of Search ............ 260/990, 606.5 P, 969, 260/976, 982

[56]  References Cited

OTHER PUBLICATIONS

Huben–Weyl, Methoden der Organischen Chemie, vol. XII/I, p. 158 and vol. XII/2, p. 310, (1964).

*Primary Examiner*—Richard L. Raymond
*Attorney, Agent, or Firm*—Burgess, Dinklage & Sprung

[57]  ABSTRACT

A process for the purification of a phosphorus oxy compound selected from the group consisting of phosphoric, phosphonic and phosphinic acid esters and phosphine oxides, comprising mixing the impure phosphorus oxy compounds with an oxidizing agent, subsequently reacting the mixture with at least one of water and an alcohol, and separating the purified phosphorus oxy compound. The oxidizing agent may be any of those known in the art including chlorine, bromine, iodine, and carbon tetrachloride plus a base. Oxidation can be effected in aqueous media and/or the product washed in aqueous media to neutrality.

6 Claims, No Drawings

PRODUCTION OF PHOSPHORUS OXY COMPOUNDS

This invention relates to a process for the purification of phosphoric, phosphonic and phosphinic acid esters and phosphine oxides, hereinafter referred to generically as phosphorus compounds, more especially phosphorus compounds of the type suitable for use as extractants.

In practice, the use, for example as extractants, of these phosphorus compounds obtainable by known processes can give rise to difficulties reflected in extremely long phase separation times. These difficulties cannot be eliminated by conventional methods such as, for example, changing the diluent or using pulsating packed columns instead of mixers and settlers. In some cases, deposits are even formed at the phase interface, making phase separation particularly difficult.

Difficulties of this kind occur above all in cases where the above-mentioned phosphorus compounds have been produced by way of a trivalent phosphorus stage. Although the nature of the troublesome impurities cannot always be determined, it may nevertheless be assumed that they consist of phosphorus compounds of an intermediate valency stage. According to the literature (P. Markl, Extraktion und Extraktionschromatographie in der anorg. Analytik, Akad. Verlagsgesellschaft, Frankfurt/Main, 1972, pages 117 and 118), neutral phosphorus compounds are purified by multistage washing with acids (to hydrolyze the pyrophosphorus compounds) and alkalis (to wash out the acid esters) and by repeated distribution between carbon tetrachloride and water or by vacuum distillation.

Distillation of the long-chain phosphorus compounds, which are suitable for extraction purposes, is difficult on account of thermal decomposition. Purification of the phosphorus compounds by repeated distribution between carbon tetrachloride and water is hardly suitable for industrial application on account of the large number of stages required.

The third group of known purification processes is based on the differing sensitivity to hydrolyzing reagents between the phosphorus compounds to be purified on the one hand and the impurities to be removed on the other hand. Processes of this kind are only suitable for removing readily hydrolyzable impurities. Impurities which are difficult to hydrolyze have to be treated with acids and alkalis, in some cases for such long periods that hydrolysis of the ester groups in phosphoric, phosphonic and phosphinic acid esters can result in considerable losses of yield.

Attempts to purify pentane phosphonic acid dipentyl ester by heating with 3-normal hydrochloric acid for 10 hours to 90° C, followed by washing with 0.5-normal sodium hydroxide, have shown that the impurities formed during synthesis would appear to be comparable in their resistance to hydrolysis with the ester groups present in the product. Although 18% of the pentane phosphonic acid dipentyl ester are hydrolyzed by this treatment, the residual product still contains impurities which cause excessively long phase separation times in extraction processes.

In principle, troublesome impurities could be removed from phosphine oxides by prolonged treatment with acids and alkalis. However, this would not be practical in the case of large-scale operation. Where phosphorus acid esters are concerned, this process would result in unacceptable losses of yield.

Accordingly, the object of the present invention is to provide a suitable purification process for phosphorus compounds of this kind. Accordingly, the present invention relates to a process for the purification of phosphoric, phosphonic and phosphinic acid esters and phosphine oxides, which is distinguished by the fact that the phosphorus compounds are treated with an oxidizing agent, subsequently reacted with water and/or an alcohol, optionally in the presence of a base, after which the oxidation products are optionally separated off by known methods.

It has surprisingly been found that the impurities present in the phosphorus compounds can be readily and completely removed in this way.

Suitable oxidizing agents are, for example, chlorine, bromine, iodine or oxyacids of these elements, and also their salts. Suitable salts are, for example, Na-hypochlorite, Na-chlorate, N-bromate and Na-iodate. Instead of using the Na-salts, it is of course also possible to use other soluble salts. Chromates, permanganates, peroxides, peroxo salts and nitrous gases are also suitable. Another suitable oxidizing agent is, for example, even carbon tetrachloride in the presence of bases. The troublesome impurities may be oxidized in the presence or absence of water, e.g. up to about 500% and especially about 50 to 200% by weight of water based on the weight of the phosphorus material to be purified, at pH-values in the range of from 0 to 14 and at temperatures in the range of from about −10° to 150° C and preferably in the range of about 0° to 100° C, especially 20° to 80° C.

The phosphorus compounds thus treated may be worked up as follows:

a. The oxidation products of the impurities may be partly or completely esterified by reaction with stoichiometric quantities, but preferably with excess quantities, of an alcohol, optionally in the presence of a base.

b. The oxidation products of the impurities may be washed out of the phosphorus compounds after esterification with an alcohol, or without esterification, with water, preferably in the presence of alkalis, over the entire temperature range where water is in liquid state, preferably at temperatures in the range of about 15° to 100° C.

Although the reaction mechanism has not been investigated in all its details, it may be assumed that impurities containing the phosphorus in an intermediate valency stage are converted by chlorine, bromine, iodine or carbon tetrachloride into compounds with a phosphorus-halogen bond. Under the effect of other oxidizing agents, the troublesome impurities are probably directly oxidized into structures such as P—OH or P—O—P. It is known that these oxidation products of the impurities can be esterified with alcohols, albeit in different yields. Under the effect of water, these oxidation products are hydrolyzed into acids which are soluble in water in the form of their salts, preferably their alkali metal or ammonium salts.

It is a known fact that phosphorus-halogen compounds can be more effectively esterified with alcohols than compounds containing P—OH— or P—O—P— groups. In cases where the oxidized impurities are to be esterified with an alcohol, it is best, although not absolutely essential, to use dry halogens as the oxidizing agent so that the impurities are oxidized into phosphorous-halogen compounds.

In principle, the process according to the invention may be used for all the aforementioned classes of phosphorus compounds. It is preferably used for substances which are difficult to purify by distillation corresponding to the general formula:

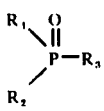

in which the radicals $R_1$, $R_2$ and $R_3$, which may be the same of different, each represents a linear or branched, optionally substituted aliphatic hydrocarbon radical or an optionally substituted araliphatic or aromatic hydrocarbon radical with up to 18 carbon atoms, in addition to which one or more of these radicals may be attached to the phosphorus through an oxygen atom.

The following are examples of phosphorus compounds of this kind: tributylphosphate, tripentylphosphate, tris-[2-ethylhexyl]-phosphate, butane phosphonic acid dibutyl ester, n-pentane phosphonic acid-di-[n-pentyl]-ester, n-pentane phosphonic acid-di-[isopentyl ester], n-pentane phosphonic acid-n-pentylisopentyl ester, iso-pentane phosphonic acid-di-[n-pentyl]-ester, iso-pentane phosphonic acid-n-pentyl-isopentyl-ester, iso-pentane phosphonic acid-di-[isopentyl]-ester, n-pentane phosphonic acid-di-[n-hexyl]-ester, n-hexane phosphonic acid-di-[n-pentylester], dioctyl phosphinic acid butyl ester, dioctyl phosphinic acid isobutyl ester, 1-oxo-1-[2-ethylhexyl]-oxy-phospholine, trihexyl phosphine oxide, tris-[2-ethylhexyl]-phosphine oxide, trioctyl phosphine oxide and tridecyl phosphine oxide.

The process according to the invention is illustrated by the following Examples. The following tests were used for determining the quality of the phosphorus compounds:

a. Short-term test

A 1- to 2- molar solution in commercial-grade xylene of the phosphorus compound to be tested was shaken three times for 10 minutes with the same volume of a fresh solution of the following composition:
$Fe^{3+}$ — 2.5 g/l
$Cu^{2+}$ — 20 g/l
$Zn^{2+}$ — 36 g/l
$H^+$ — 2.9 g/l
$Cl^-$ — 132 g/l
$SO_4^{2-}$ — 55 g/l The organic phase obtained was then washed 4 to 5 times by shaking for 10 minutes with the same volume of water.

A few, obviously very heavily contaminated phosphorus compounds did not form clearly separated phases even after shaking for 10 minutes with the metal salt solution. These preparations formed deposits during the subsequent washes with water.

Although no deposits were formed in the case of less heavily contaminated phosphorus compounds, the phase separation times were nevertheless increased in length during each wash with water, and the phases no longer separated clearly over a period of 10 minutes by the fifth wash at the latest.

As a result of brief shaking (approximately 10 minutes) of the impure phosphorus compounds with dilute sodium hydroxide and repeated washing with water, most of the phosphorus compounds tested subsequently produced rapid phase separation in this short-term test.

b. Long-term test

However, when the phosphorus compounds were shaken with the acid metal salt solution for 8 hours ("long-term test") and not just for 10 minutes, as in the "short-term test", the same problems, such as slow phase separation, and in some cases even deposit formation, were again encountered during subsequent washing with water, even in the case of products which had passed the short-term test after washing with NaOH.

The short-term test may be regarded as an "instant check," while the long-term test may be regarded as the actual purity check.

EXAMPLE 1

Commercial-grade $POCl_3$, which had been produced by the oxidation of $PCl_3$ and which still contained 1.2% of $PCl_3$, was esterified with a commercial-grade mixture of n-pentanol and 2-methyl butanol in accordance with the literature (Houben-Weyl, Methoden der organischen Chemie, Vol XII/2, pages 310 et seq, G. Thieme Verlag Stuttgart, 1964). According to analysis by gas chromatography, the resulting tripentyl phosphate contained 1.1% of dipentyl phosphite.

Even the short-term test showed that this product was not sufficiently pure for the extraction of metals. Phase separation after the third wash of the metal-laden organic phase with water lasted more than 15 minutes.

A mixture of equal volumes of 2-molar sodium hypochlorite solution and 2-molar sodium hydroxide was added dropwise with vigorous stirring at 80° C to 500 g of this crude tripentyl phosphate and 500 g of water. The oxidizing agent mixture was added until, 5 minutes after the last drop had been added, it could still be detected with KI-starch paper.

Following separation of the aqueous phase, the organic phase was washed twice for 30 minutes at 80° C with twice the volume of water, accompanied by the dropwise addition of sodium hydroxide up to pH 8.5 - 9.5.

The organic phase was then washed with water at 80° C until it showed a neutral reaction. The product was dried at 95° C/2-3 mm Hg.

A product satisfying the requirements of tests (a) and (b) was obtained.

EXAMPLE 2

According to gas chromatography, crude pentane phosphonic acid dipentyl ester, obtained by the rearrangement of tripentyl phosphite, contained 0.5% of tripentyl phosphite, 3% of dipentyl phosphite and 3 unidentifiable impurities in quantities of from 0.1 to 0.2%. 1.5 kg of this crude product were saturated with chlorine at 0° C until it remained yellow in color. Thereafter the mixture was degassed at 2-3 mm Hg and divided into three equal parts.

a. 500 g of pentanol were introduced into a stirrer-equipped flask. One part of the crude product previously oxidized with chlorine was then added with stirring at a temperature of 20° to 40° C. After stirring for 40 minutes, the mixture was washed twice with 500 ml of 6NHCl, subsequently neutralized with NaHCO₃ and the excess pentanol distilled off at 2 to 3 mm Hg.

b. Another part of the oxidized crude product was introduced dropwise with rapid stirring into 1 liter of boiling water and subsequently kept for 1 hour at 100° C. The organic phase was twice heated while stirring for 20 minutes to 80° C with 2 1-liter portions of 0.1 NaOH solution and thereafter washed with water until it showed a neutral reaction. The product was dried at 95° C/2-3 mm Hg.

c. The procedure was as in test 2 b), except that the oxidized crude product was not added dropwise to boiling water, but instead to a 0.1 molar soda solution which had been heated to 80° C.

EXAMPLE 3

Chlorine was introduced at 80° C into a mixture of 0.5 kg of crude pentane phosphonic acid dipentyl ester and 0.5 kg of water until the mixture remained yellow in color. The organic phase was separated off and worked up in accordance with 2 c).

EXAMPLE 4

The procedure was as described in Example 3, except that liquid bromine was added dropwise as the oxidizing agent.

EXAMPLE 5

50 g of dioctyl phosphinic acid butyl ester,

obtained by reacting dioctyl phosphinic acid with tributyl phosphite and distilling off most of the dibutyl phosphite formed, was mixed with a solution of 0.5 g of K₂Cr₂O₇ and 20 ml of concentrated HCl, and the resulting mixture was heated for 10 minutes to 80° C. The organic phase was then washed at 80° C,
once for 5 minutes with 50 ml of 1NHCl,
twice for 5 minutes with 100 ml of 0.5 NNaOH
and finally with water until a neutral reaction was obtained.

EXAMPLE 6

Tris-(2-ethylhexyl)-phosphine oxide was produced from commercial-grade phosphorus oxychloride and 2-ethyl hexyl magnesium chloride in accordance with the literature (Houben-Weyl, Methoden der organischen Chemie, Vol. XII/1, pages 158 et seq. G. Thieme Verlag Stuttgart, 1964). The starting materials were used in a molar ratio of POCl₃ to RMgCl of 1 : 3. N/10 KMnO₄-solution was added at room temperature, in the presence of 50 ml of 1 NH₂SO₄, to 50 g of the product obtained until one drop of this solution was not completely deprived of color after a period of 5 minutes. The organic phase was washed at 80° C,
twice with 50 ml of 1-molar H₂SO₄
twice with 50 ml of 1-normal NaOH
and then with water until a neutral reaction was obtained.

EXAMPLE 7

50 g of tris-(2-ethylhexyl)-phosphine oxide were added dropwise at 60° C to 100 ml of fuming nitric acid. After stirring for 15 minutes, 200 ml of water were added, the aqueous phase was separated off and the organic product was washed at 80° twice with 100 ml of 2-normal NaOH and then with water until it showed a neutral reaction.

EXAMPLE 8

200 g of butane phosphonic acid dibutyl ester,

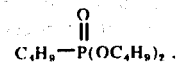

were purified by method 2 c). The purified product was distilled over without fractionation at 1 mm Hg.

EXAMPLE 9

An aqueous mixture of 0.1 mole/l of KMnO₄ and 0.4 mole/l H₂SO₄ was added with stirring to crude pentane phosphonic acid dipentyl ester (200 g) containing 20% of dipentyl phosphite until the aqueous phase was permanently colored. The product phase was then washed
once with 1 NH₂SO₄ (ratio by volume 1 : 1)
twice with water at 80° C, accompanied by the dropwise
addition of sodium hydroxide to pH 9-10 (ratio by volume of product to water 1 : 1),
and finally several times with water until a neutral reaction was obtained.

The product was dried at 95° C/2-3 mm Hg.

EXAMPLE 10

Crude pentane phosphonic acid dipentyl ester (50 g) containing 20% of dipentyl phosphite was mixed with anhydrous soda (15 g), water (50 g) and 30% hydrogen peroxide (15 g). The mixture was heated with vigorous stirring first for 30 minutes at room temperature and then for 15 minutes at 80° C. The organic product was then stirred for 30 minutes at 80° C with the same volume of water, accompanied by the dropwise addition of sodium hydroxide to pH 9 - 10. Finally, the organic product was washed with water until it showed a neutral reaction. The product was dried at 95° C/2-3 mm Hg.

EXAMPLE 11

The size of the test batch and the procedure were the same as in the preceding Example. The only difference was that 15 g of 10% sulfuric acid were added instead of 15 g of anhydrous soda.

EXAMPLE 12

The size of the test batch and the procedure were the same as in the preceding example. However, 15 g of K₂S₂O₈ were used instead of hydrogen peroxide as the oxidizing agent.

EXAMPLE 13

20% sodium hydroxide was added dropwise with stirring at 80° C to crude pentane phosphonic acid dipentyl ester (100 g) containing 20% of dipentyl phosphite and carbon tetrachloride (100 g). The mixture began to boil under the effect of the heat of reaction. On completion of the exothermic reaction, the mixture was kept for 20 minutes at pH 9-10 and at 80° C.

The organic product was washed twice at 80° C with the same volume of water, accompanied by the addition of sodium hydroxide up to pH 9-10. After several washes with water until it showed a neutral reaction, the product was dried at 95° C/2-3 mm Hg.

In all the compounds purified in accordance with the preceding examples, the conditions of the above-described tests were satisfied.

It will be appreciated that the instant specification and examples are set forth by way of illustration and not limitation, and that various modifications and changes may be made without departing from the spirit and scope of the present invention.

What is claimed is:

1. A process for the purification of a phosphorus oxy compound selected from the group consisting of phosphoric, phosphonic and phosphinic acid esters and phosphine oxides containing impurities comprising phosphorus compounds of an intermediate valency stage, comprising mixing the impure phosphorus oxy compounds with an oxidizing agent, subsequently reacting the mixture with at least one of water and an alcohol, and separating the purified phosphorus oxy compound.

2. A process as claimed in claim 1, wherein the oxidizing agent is selected from the group consisting of chlorine, bromine or iodine and is employed at a temperature in the range of about −10° to +150° C.

3. A process as claimed in claim 2, wherein the oxidizing agent is mixed with the phosphorus oxy compound at a temperature in the range of about 20° to 80° C, the mixture is reacted with an alcohol and thereafter combined with water, and the aqueous phase and any excess unreacted alcohol is removed to leave the purified phosphorus oxy compound.

4. A process as claimed in claim 1, wherein a mixture of carbon tetrachloride and a base is used as the oxidizing agent.

5. A process as claimed in claim 1, wherein oxidation is carried out in the presence of from 0 to about 500% by weight of water based on the weight of the phosphorus oxy compound to be purified.

6. A process as claimed in claim 5, wherein oxidation is effected in the presence of about 50 to 200% by weight of water based on the weight of the phosphorus oxy compound to be purified, the aqueous phase is separated from the organic phase, the organic phase is washed with an aqueous solution to substantial neutrality, and the aqueous solution is removed from the purified phosphorus oxy compound.

* * * * *